US005741788A

United States Patent [19]

Olesen et al.

[11] Patent Number: 5,741,788
[45] Date of Patent: Apr. 21, 1998

[54] HETEROCYCLIC COMPOUNDS AND THEIR PREPARATION AND USE

[75] Inventors: Preben H. Olesen, København NV; Per Sauerberg, Farum, both of Denmark

[73] Assignee: Novo Nordisk A/S, Bagsvaerd, Denmark

[21] Appl. No.: 559,961

[22] Filed: Nov. 17, 1995

[30] Foreign Application Priority Data

Nov. 21, 1994 [DK] Denmark ................... 1324/94

[51] Int. Cl.$^6$ ............... C07D 513/14; C07D 513/04; A61K 31/425; A61K 31/44
[52] U.S. Cl. .............. 514/183; 514/286; 514/293; 540/477; 546/63; 546/83
[58] Field of Search ............... 548/126, 127, 548/134; 546/83, 63; 540/522, 521, 477; 514/183, 362, 293, 286

[56] References Cited

U.S. PATENT DOCUMENTS 4,217,356  8/1980  Neumann ................ 424/270
5,171,861  12/1992  Ernhoffer et al. ............ 548/142

FOREIGN PATENT DOCUMENTS 0 074 741  3/1983  European Pat. Off. .
0 216 247  4/1987  European Pat. Off. .
4338761  11/1992  Japan .
1122659  11/1984  U.S.S.R. .
WO 92/03433  3/1992  WIPO .

OTHER PUBLICATIONS

Girard et al., J. Med. Chem., vol. 32, pp. 1566–1571 (1989).
Sauerberg et al., J. Med. Chem., vol. 35, pp. 2274–2283 (1992).

Primary Examiner—Mukund J. Shah
Assistant Examiner—Deepak R. Rao
Attorney, Agent, or Firm—Steve T. Zelson; Elias J. Lambiris

[57] ABSTRACT

The present invention relates to therapeutically active azacyclic or azabicyclic compounds, a method of preparing the same and to pharmaceutical compositions comprising the compounds. The novel compounds are useful in treating diseases in the central nervous system caused by malfunctioning of the muscarinic cholinergic system.

26 Claims, No Drawings

HETEROCYCLIC COMPOUNDS AND THEIR PREPARATION AND USE

This application claims priority of Danish application 1324/94 filed Nov. 21, 1994, which is incorporated herein by reference.

FIELD OF THE INVENTION

The present invention relates to therapeutically active compounds, a method of preparing the same and to pharmaceutical compositions comprising the compounds. The novel compounds are cholinergic muscarinic ligands useful as stimulants of the cognitive function of the forebrain and hippocampus of mammals and especially in the treatment of Alzheimer's disease.

BACKGROUND OF THE INVENTION

Due to the in general improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, then the postsynaptic muscarinic receptors in the forebrain and hippocampus still exist. Therefore muscarinic cholinergic agonists are useful in the treatment of Alzheimer's disease in halting progression of Alzheimer's disease, and in improving the cognitive functions of elderly people.

The compounds of this invention are also useful analgesic agents and therefore useful in the treatment of severe painful conditions.

Furthermore, the compounds of this invention are useful in the treatment of glaucoma, schizophrenia or schizophreniform conditions, anxiety, depression, sleeping disorders, epilepsy, cerebral ischemia, gastrointestinal motility disorders and urinary bladder dysfunctions.

In J. Med. Chem. 1989, 32, 1566–1571 the compound 6,7,8,9-tetrahydro[1,2,5]thiadiazolo[3,4-h]isoquinoline is described as a phenylethanolamine-N-methyltransferase (PNMT) inhibitor.

SUMMARY OF THE INVENTION

The novel compounds of the invention are heterocyclic compounds of formula I selected from the following

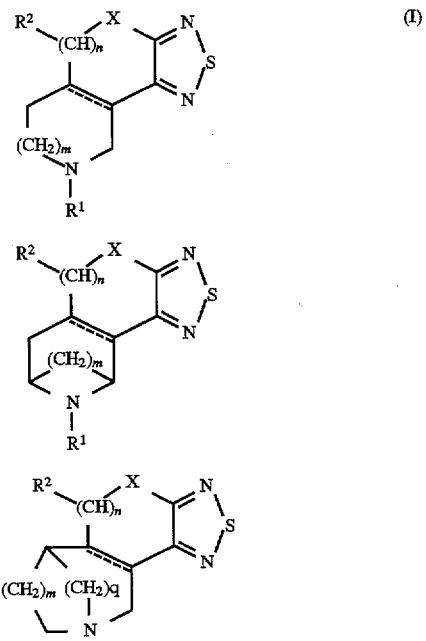

wherein
X is $-CH_2-$, $-O-$, $-S-$, $=C-$ or $-N(R^3)-$; and
m is 0, 1 or 2; and
n is 0, 1 or 2; and
q is 0, 1 or 2; and
$R^1$ is H, straight or branched $C_{1-5}$-alkyl, straight or branched $C_{2-5}$-alkenyl, straight or branched $C_{2-5}$-alkynyl, $C_{3-6}$-cycloalkyl or $C_{3-6}$-cycloalkyl$C_{1-3}$-alkyl; and
$R^2$ and $R^3$ independently are H, straight or branched $C_{1-10}$-alkyl, straight or branched $C_{2-10}$-alkenyl, straight or branched $C_{2-10}$-alkynyl, phenyl optionally substituted with halogen, $CF_3$, CN, $NO_2$, OH, $C_{1-4}$-alkyl, $C_{1-4}$-alkoxy or $SO_2R^4$ wherein $R^4$ is $C_{1-4}$-alkyl, or $C_{1-5}$-alkyl, $C_{2-5}$-alkenyl or $C_{2-5}$-alkynyl each of which is substituted with halogen, $CF_3$, $OCF_3$, CN, $C_{3-6}$-cycloalkyl or phenyl which phenyl is optionally substituted with halogen, $CF_3$, $OCF_3$, CN, $NO_2$, OH, $C_{1-4}$-alkyl, $C_{1-4}$-alkoxy or $SO_2R^4$; and ---- is a single or double bond; or a pharmaceutically acceptable salt thereof, provided that when the compounds of formula I are

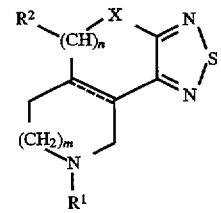

and when $R^1$ and $R^2$ both are H and n and m are 1 then X is $-CH_2-$, $-O-$, $-S-$ or $-N(R^3)-$.

DETAILED DESCRIPTION OF THE INVENTION

The terms "$C_{1-n'}$-alkyl" wherein n' can be from 2 through 10, as used herein, represent a branched or linear alkyl group having from one to the specified number of carbon atoms. Typical $C_{1-6}$-alkyl groups include, but are not limited to, methyl, ethyl, n-propyl, iso-propyl, butyl, iso-butyl, sec-butyl, tert-butyl, pentyl, hexyl and the like.

The terms "$C_{2-n'}$-alkenyl" wherein n' can be from 3 through 10, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, pentenyl, hexenyl and the like.

The terms "$C_{2-n'}$-alkynyl" wherein n' can be from 3 through 10, as used herein, represents an usaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The terms "$C_{3-n}$-cycloalkyl" wherein n=4-6, represents cyclopropyl, cyclobutyl, cyclopentyl, cyclohexyl and the like. The term "$C_{3-6}$-cycloalkyl$C_{1-3}$-alkyl" and the term "$C_3$cycloalkyl$C_{1-2}$alkyl" represent an alkyl group substituted at a terminal carbon with respectively a $C_{3-6}$-cycloalkyl group and a $C_{1-2}$-cycloalkyl group. Typical cycloalkylalkyl groups include cyclopropylmethyl, cyclopropylethyl, cyclohexylethyl, cyclohexylmethyl, 3-cyclopentylpropyl, and the like.

The terms $C_{1-n''}$-alkoxy" wherein n" can be from 2 through 4, as used herein, alone or in combination, refers to a monovalent substituent comprising a lower alkyl group linked through an ether oxygen having its free valence bond from the ether oxygen and having from 1 to the specified number of carbon atoms e.g. methoxy, ethoxy, propoxy, butoxy and the like.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in Journal of Pharmaceutical Science, 66, 2 (1977) which are hereby incorporated by reference.

The invention also relates to methods of preparing the above mentioned compounds, comprising a) reacting a compound of formula II selected from the following

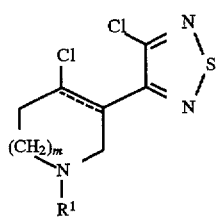

(II)

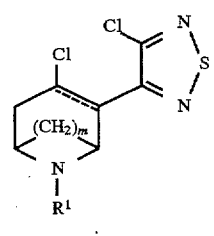

wherein m, n, q, $R^1$ and ⋯ are defined as above with NaSH to form a compound of formula III (III)

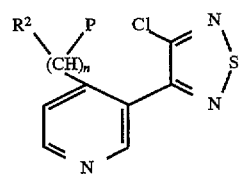

wherein m, n, q, $R^1$ and ⋯ are defined as above, or b) reacting a compound of formula IV (IV)

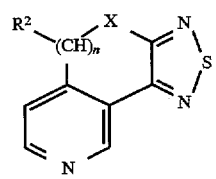

wherein $R^2$ and n are defined as above and P is halogen with NaSH, OH⁻ or $NH_2R^3$, wherein $R^3$ is as defined above, to form a compound of formula V (V)

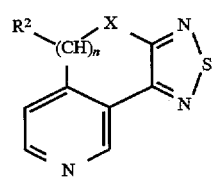

wherein $R^2$ and n are as defined above and X is S, O or $NR^3$, which compound is reacted with first an alkyl halide and subsequently with $NaBH_4$ to form a compound of formula VI (VI)

wherein $R^1$, $R^2$, n and X are as defined above, or c) reacting a compound of formula VII $$\text{(VII)}$$

wherein $R^1$, $R^2$, n, m, q, ...... and P are as defined above with NaSH, OH⁻ or $NH_2R^3$, wherein $R^3$ is as defined above, to form a compound of formula VIII $$\text{(VIII)}$$

wherein $R^1$, $R^2$, m, n, q ...... and X are as defined above.

It is to be understood that the invention extends to each of the stereoisomeric forms of the compounds of formula I as well as the racemates.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-Oxo labels muscarinic receptor in the CNS (with a preference for agonist domains of the receptors). Three different sites are labelled by $^3$H-Oxo. These sites have affinity of 1.8, 20 and 3000 nM, respectively. Using the present experimental conditions only the high and medium affinity sites are determined.

The inhibitory effects of compounds on $^3$H-Oxo binding reflects the affinity for muscarinic acetylcholine receptors.

All preparations are performed at 0°-4° C. unless otherwise indicated. Fresh cortex (0.1-1 g) from male Wistar rats (150-250 g) is homogenized for 5-10 s in 10 ml 20 mM Hepes pH: 7.4, with an Ultra-Turrax homogenizer. The homogenizer is rinsed with 10 ml of buffer and the combined suspension centrifuged for 15 min. at 40,000×g. The pellet is washed three times with buffer. In each step the pellet is homogenized as before in 2×10 ml of buffer and centrifuged for 10 min. at 40,000×g.

The final pellet is homogenized in 20 mM Hepes pH: 7.4 (100 ml per g of original tissue) and used for binding assay. Aliquots of 0.5 ml is added 25 ul of test solution and 25 ul of $^3$H-Oxotremorine (1.0 nM, final concentration) mixed and incubated for 30 min. at 25° C. Non-specific binding is determined in triplicate using arecoline (1 ug/ml, final concentration) as the test substance. After incubation samples are added 5 ml of ice-cold buffer and poured directly onto Whatman GF/C glass fiber filters under suction and immediately washed 2 times with 5 ml of ice-cold buffer. The amount of radioactivity on the filters are determined by conventional liquid scintillation counting. Specific binding is total binding minus non specific binding.

Test substances are dissolved in 10 ml water (if necessary heated on a steam-bath for less than 5 min.) at a concentration of 2.2 mg/ml. 25–75% inhibition of specific binding must be obtained before calculation of $IC_{50}$.

The test value will be given as $IC_{50}$ (the concentration (nM) of the test substance which inhibits the specific binding of $^3$H-Oxo by 50%).

$IC_{50}$=(applied test substance concentration)×$(C_x/C_o-C_x)$ nM where $C_o$ is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$H-PRZ (pirenzepine, [N-methyl-$^3$H]) binding to rat cerebral cortex membranes. Pirenzepine binds selectively to subtype of muscarinic receptors. Historically the type is named the $M_1$-site, whereas pirenzepine sensitive site would be more appropriate. Although selective for $M_1$-sites pirenzepine also interact with $M_2$-sites.

All preparations are performed at 0°-4° C. unless otherwise indicated. Fresh cortex (0.1-1 g) from male Wistar rats (150-200 g) is homogenized for 5-10 s. in 10 ml 20 mM Hepes pH: 7.4, with an Ultra-Turrax homogenizer. The homogenizer is rinzed with 2×10 ml of buffer and the combined suspension centrifuged for 15 min at 40,000×g. The pellet is washed three times with buffer. In each step the pellet is homogenized as before in 3×10 ml of buffer and centrifuged for 10 min at 40,000×g.

The final pellet is homogenized in 20 mM Hepes pH: 7.4 (100 ml per g of original tissue) and used for binding assay. Aliquots of 0.5 ml is added 20 µl of test solution and 25 µl of $^3$H-Pirenzepine (1.0 nM, final conc.), mixed and incubated for 60 min at 20° C. Non-specific binding is determined in triplicate using atropine (1 µg/ml, final conc.) as the test substance. After incubation samples are added 5 ml of ice-cold buffer and poured directly onto Whatman GF/C glass fiber filters inder suction and immediately washed 2 times with 5 ml of ice-cold buffer. The amount of radioactivity on the filters are determined by conventional liquid scintillation counting. Specific binding is total binding minus non-specific binding.

Test substances are dissolved in 10 ml water, at a concentration of 0.22 mg/ml. 25–75% inhibition of specific binding must be obtained before calculation of $IC_{50}$.

The test value will be given as $IC_{50}$ (the concentration (nM) of the test substance which inhibits the specific binding of $^3$H-PRZ by 50%).

$IC_{50}$=(applied test substance concentration)×$(C_x/C_o-C_x)$ nM where $C_o$ is specific binding in control assays and $C_x$ is the specific binding in the test assay. (The calculations assume normal mass-action kinetics).

Test results obtained by testing some compounds of the present invention will appear from the following table 1.

TABLE 1

| Compound | $^3$H-Oxo-M $IC_{50}$, ng/ml | $^3$H-Pz $IC_{50}$, nM |
| --- | --- | --- |
| 1 | 270 | >1000 |
| 2 | 6.4 | 284 |
| 3 | 2.2 | 26 |
| 4 | 14 | 255 |
| 5 | 14 | 80 |

The compounds of the invention are effective over a wide dosage range. For example, in the treatment of adult humans, dosages from about 0.05 to about 100 mg, preferably from about 0.1 to about 100 mg, per day may be used. A most preferable dosage is about 10 mg to about 70 mg per day. In choosing a regimen for patients suffering from diseases in the central nervous system caused by malfunctioning of the muscarinic cholinergic system it may frequently be necessary to begin with a dosage of from about 30 to about 70 mg per day and when the condition is under control to reduce the dosage as low as from about 1 to about 10 mg per day. The exact dosage will depend upon the mode of administration, form in which administered, the subject to be treated and the body weight of the subject to be treated, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intraurethral, intramuscular, intranasal, ophthalmic solution or an ointment, the oral route being preferred.

Typical compositions include a compound of formula I or a pharmaceutically acceptable acid addition salt thereof, associated with a pharmaceutically acceptable carrier. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 1 to about 100 mg in a pharmaceutically acceptable carrier per unit dosage.

A typical tablet, appropriate for use in this method, may be prepared by conventional tabletting techniques and contains:

| | |
|---|---|
| Active compound | 5.0 mg |
| Lactosum | 67.8 mg Ph. Eur. |
| Avicel ® | 31.4 mg |
| Amberlite ® | 1.0 mg |
| Magnesii stearas | 0.25 mg Ph. Eur. |

The invention will now be described in further detail with reference to the following examples:

EXAMPLE 1

A. 3-Chloro-2-(3-chloro-1,2,5-thiadiazol-4-yl)-8-azabicyclo[3.2.1]oct-2-ene

To a solution of 8-ethoxycarbonyl-3-chloro-2-(3-chloro-1,2,5-thiadiazol-4-yl)-8-azabicyclo[3.2.1]oct-2-ene (1.7 g, 5 mmol) (PCT/DK91/00236) in dry toluene (50 ml) was added aluminium trichloride (2.6 g, 20 mmol). The reaction mixture was heated to 80° C. and kept at this temperature for 10 min. After cooling water was carefully added to the reaction mixture. The water solution was extracted with methylene chloride (2×50 ml), then made basic with 4N sodiumhydroxide solution. The alkaline solution was extracted with diethylether (3×100 ml). The organic extracts from the basic extractions were dried over magnesium sulfate and evaporated. The residue was crystallized as the oxalate salt from acetone in 1.60 g yield.

B. 8-Methyl-2-(3-chloro-1,2,5-thiadiazol-4-yl)-3-chloro-8-azabicyclo[3.2.1]oct-2-ene A mixture of 3-chloro-2-(3-chloro-1,2,5-thiadiazol-4-yl)-8-azabicyclo[3.2.1]oct-2-ene (1.0 g, 3.8 mmol), formaldehyde (37% water solution, 10 ml) and formic acid (6.0 ml) was heated at reflux for 2 h. After cooling water was added (100 ml) and the water solution was made basic with potassium carbonate. The water solution was extracted with diethylether (3×50 ml). The organic extracts were dried over magnesium sulfate and evaporated. The residue was crystallized as the oxalate salt from acetone in 1.2 g yield.

C. 6,8-Ethano-7-methyl-5,6,7,8-tetrahydro-1,2,5-thiadiazolo[3',4':4,5]thieno[3,2-c]pyridine oxalate To a solution of 8-methyl-2-(3-chloro-1,2,5-thiadiazol-4-yl)-3-chloro-8-azabicyclo[3.2.1]oct-2-ene (276 mg, 1.0 mmol) in dimethylformamide (20 ml) was added sodium hydrogensulfide monohydrate (296 mg, 4 mmol). The reaction mixture was stirred at room temperature for 3 h. Water (150 ml) was added and the solution made acidic with concentrated hydrochloric acid. The water solution was extracted with diethylether (2×100 ml), then made basic with solid potassium carbonate. The alkaline solution was extracted with diethylether (3×100 ml). The organic extracts from the basic extractions were dried over magnesium sulfate and evaporated. The residue was crystallized as the oxalate salt from acetone in 160 mg yield. M.p. 212°–213° C. (Compound 1).

EXAMPLE 2

A. 1-Benzoyl-4-chloro-3-(3-chloro-1,2,5-thiadiazol-4-yl)-1,2,5,6-tetrahydropyridine To a solution of 1-benzoyl-3-formyl-4-chloro-1,2,5,6-tetrahydropyridine (EP 316718) (42.5 g, 170 mmol) and acetic acid (11.0 g, 170 mmol) in ethanol (100 ml) was added potassium cyanide (12.0 g, 170 mmol) dissolved in water (20 ml). The reaction mixture was stirred overnight at room temperature. The precipitated compound was filtered and suspended in water (100 ml). Ammonium chloride (10.0 g, 170 mmol), ammoniumhydroxide (25% in water, 25 ml) and ethanol (100 ml) were added. The reaction mixture was stirred at room temperature for 7 h. Additional water (200 ml) was added and the water phase was extracted with diethylether (3×200 ml). The organic extracts were dried over magnesium sulfate and evaporated. The residue was dissolved in dimethylformamide (100 ml) and slowly added to a solution of sulfurmonochloride (25 ml) in dimethylformamide (25 ml) at 0° C. The reaction mixture was slowly heated to room temperature and stirred at this temperature for another 8 h. Water (50 ml) was carefully added and the precipitated sulfur was removed by filtration. Additional water (500 ml) was added and the water phase was extracted with diethylether (2×200 ml). The organic extracts were dried over magnesium sulfate, filtered and evaporated. The residue was purified by column chromatography, eluent:

methylene chloride/ethyl acetate: 20/1. Evaporation of the fractions containing the wanted product gave 7.4 g of the title compound.

B. 7-Benzoyl-5,6,7,8-tetrahydro-1,2,5-thiadiazolo[3', 4':4,5]thieno[3,2-c]pyridine To a solution of 1-benzoyl-4-chloro-3-(3-chloro-1,2,5-thiadiazol-4-yl)-1,2,5,6-tetrahydropyridine (3.4 g, 10 mmol) in dimethylformamide was added sodiumhydrogensulfide monohydrate (1.5 g, 20 mmol) and potassium carbonate (2.0 g). The reaction mixture was stirred at room temperature for 3 h. Water (500 ml) was added and the water phase was extracted with diethylether (2×15 ml). The organic extracts were dried over magnesium sulfate, filtered and evaporated. The residue was purified by column chromatography, eluent: methylene chloride/ethyl acetate: 10/1, giving the title compound in 2.1 g yield.

C. 5,6,7,8-Tetrahydro-1,2,5-thiadiazolo[3',4':4,5]thieno[3,2-c]pyridine oxalate A suspension of 7-benzoyl-5,6,7,8-tetrahydro-1,2,5-thiadiazolo[3',4':4,5]thieno[3,2-c]pyridine (600 mg, 2 mmol) in concentrated hydrochloric acid (10 ml) was heated at reflux for 16 h. The reaction mixture was diluted with water (100 ml) and made alkaline with a 4N sodiumhydroxide solution. The water phase was extracted with diethylether (3×75 ml). The organic extracts were dried over magnesium sulfate, filtered and evaporated. The residue was crystallized as the oxalate salt from acetone giving the title compound in 300 mg yield. M.p. 209°–210° C. (Compound 2).

EXAMPLE 3

5,9-Methano-5,6,7,8,9,10-hexahydro-1,2,5-thiadiazolo[3',4':4,5]thieno[3,2-c]azocine oxalate To a solution of 4-chloro-3-(3-chloro-1,2,5-thiadiazol-4-yl)-1-azabicyclo[3.3.1]non-3-ene oxalate (PCT/DK91/00236) (374 mg, 1 mmol) in dimethylformamide (15 ml) was added potassium carbonate (1.0 g) and sodiumhydrogen sulfide monohydrate (296 mg, 4 mmol). The reaction mixture was stirred at room temperature for 3 h. Water (100 ml) was added and the water phase extracted with diethylether (2×100 ml). The organic phase was dried over magnesium sulfate and evaporated. The residue was crystallized as the oxalate salt from acetone. Yield: 220 mg. M.p. 220°–222° C. (Compound 3).

EXAMPLE 4

6,7,8,9-Tetrahydro[1,2,5]thiadiazolo[3,4-h]isoquinoline oxalate

This compound was prepared according to the procedure described in J. Med. Chem. 1989, 32, 1566–1571. (Compound 4).

EXAMPLE 5

A. 3-(3-Chloro-1,2,5-thiadiazol-4-yl)-4-methyl-1-phenoxycarbonyl-1,4-dihydropyridine A solution of cuprous iodide (0.40 g, 2 mmol) in dry THF (50 ml) was stirred under nitrogen for 10 min. A solution of 3-(3-chloro-1,2,5-thiadiazol-4-yl)pyridine (J.Med.Chem. 1992, 35, 2274–2283) (9.9 g, 50 mmol) in dry THF (150 ml) was added to the reaction, then cooled to −25° C. Phenylchloroformate (6.3 ml, 50 mmol) in THF (20 ml) was added slowly. The reaction mixture was stirred at −25° C. for 30 min., then allowed to warm to room temperature and stirred for another 2.5 h. The reaction mixture was cooled to −25° C. and methylmagnesium iodide (55 mmol in 20 ml ether) was added. The reaction mixture was stirred for 20 min., 20% $NH_4Cl_{(aq)}$ (100 ml) was added and then extracted with ether (200 ml). The combined organic phases were washed with 20% $NH_4Cl_{aq}$:$NH_4OH$ (1:1) (50 ml), water (50 ml), 4N HCl (50 ml), water (50 ml) and brine (50 ml). The organic phases were dried and evaporated to give crude title compound. Purification on column chromatography, eluent: toluene, gave the title compound in 11.9 g (71%) yield.

B. 3-(3-Chloro-1,2,5-thiadiazol-4-yl)-4-methylpyridine

To a solution of 3-(3-chloro-1,2,5-thiadiazol-4-yl)-4-methyl-1-phenoxycarbonyl-1,4-dihydropyridine (11.7 g, 35 mmol) in decalin (100 ml) was added sulfur (1.4 g, 43 mmol) and the reaction mixture was refluxed for 5 h. After cooling to room temperature, ether (100 ml) was added and the organic phases extracted with 1N HCl (2×75 ml). The aqueous phase was basified with $NaOH_{(aq)}$ and extracted with methylene chloride (2×100 ml). The methylene chloride phase was dried and evaporated to give solid title material in 5.47 g (74%) yield.

C. 4-Bromomethyl-3-(3-chloro-1,2,5-thiadiazol-4-yl)-pyridine

To a solution of 3-(3-chloro-1,2,5-thiadiazol-4-yl)-4-methylpyridine (0.63 g, 3 mmol) in tetrachloromethane (50 ml) was added under nitrogen, N-bromosuccinimide (0.80 g, 4.5 mmol) and α,α-azoisobutyronitril (80 mg, 0.5 mmol). The reaction mixture was stirred at 75° C. overnight. Water (50 ml) was added and after basifying with $K_2CO_3$ the reaction mixture was extracted with methylene chloride (3×100 ml). The organic phases were dried ($MgSO_4$) and evaporated. The residue contained a mixture of starting material, the monobromo and the dibromo product. Separation by column chromatography, eluent: ethyl acetate/methylene chloride: 1/10, gave the title compound in 180 mg (20%) yield.

D. [1,2,5]Thiadiazolo[3',4':2,3]thiopyrano[4,5-c]pyridine

To a solution of 4-bromomethyl-3-(3-chloro-1,2,5-thiadiazol-4-yl)pyridine (400 mg, 1.5 mmol) in DMF (20 ml) was added $NaSH.H_2O$ (80%) (150 mg, 1.8 mmol) and $K_2CO_3$. The reaction mixture was stirred at room temperature for 48 h. Water (200 ml) was added and the mixture was extracted with ether (3×50 ml). The ether phases were dried and evaporated to give crude product. Purification by column chromatography (eluent: ethyl acetate: methylene chloride (1:10)) gave the wanted product in 100 mg (32%) yield.

E. 8-Methyl-[1,2,5]thiadiazolo[3',4':2,3]thiopyrano[4,5-c]pyridinium iodide

A solution of [1,2,5]thiadiazolo[3',4':2,3]thiopyrano[4,5-c]pyridine (100 mg, 0.5 mmol) and methyliodide (1.5 mmol) in acetone (10 ml) was stirred at room temperature overnight. The precipitate was collected by filtration to give the wanted product in 120 mg (70%) yield.

F. 8-Methyl-6,7,8,9-tetrahydro[1,2,5]thiadiazolo[3',4':2,3]thiopyrano[4,5-c]pyridine oxalate To a solution of 8-methyl-[1,2,5]thiadiazolo[3',4':2,3]thiopyrano[4,5-c]pyridinium iodide (200 mg, 0.6 mmol) in ethanol (20 ml) was added NaBH₄ (76 mg, 2 mmol) at 0° C. The reaction mixture was stirred at 0° C. for 3 h. Water was added and the mixture was extracted with ether. The ether phases were dried and evaporated to give crude title material. Purification by column chromatography, eluent: ethyl acetate/methylene chloride: 1/10, gave the wanted product in 100 mg (78%) yield. Crystallization with oxalic acid in acetone gave white crystals of the title product. M.p. 144°–146° C. (Compound 5).

EXAMPLE 6

5-Phenyl-5H-8-methyl-6,7,8,9-tetrahydro[1,2,5]
thiadiazolo[3',4':2,3]thiopyrano[4,5-c]pyridine
oxalate The above mentioned compound was made in exactly the same manner as described for 8-Methyl-6,7,8,9-tetrahydro [1,2,5]thiadiazolo[3',4':2,3]thiopyrano[4,5-c]pyridine oxalate, Example 5, using benzylmagnesium bromide instead of methylmagnesium iodide (Example 5 A). M.p. 177°–178° C. (Compound 6).

We claim:

1. A compound of formula I

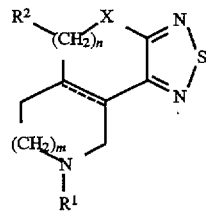

wherein

X is —S—;

m is 1;

n is 0 or 1 provided that when n is 0, $R^2$ is not present;

$R^1$ is H, straight or branched $C_{1-5}$-alkyl, straight or branched $C_{2-5}$-alkenyl, straight or branched $C_{2-5}$-alkynyl, $C_{3-6}$-cycloalkyl or $C_{3-6}$-cycloalkyl-$C_{1-3}$-alkyl; and $R^2$ is H; straight or branched $C_{1-10}$-alkyl; straight or branched $C_{2-10}$-alkenyl; straight or branched $C_{2-10}$-alkynyl; phenyl optionally substituted with halogen, $CF_3$, CN, $NO_2$, OH, $C_{1-4}$-alkyl, $C_{1-4}$-alkoxy or $SO_2R^4$ wherein $R^4$ is $C_{1-4}$-alkyl; or $C_{1-5}$-alkyl, $C_{2-5}$-alkenyl or $C_{2-5}$-alkynyl each of which is substituted with halogen, $CF_3$, $OCF_3$, CN, $C_{3-6}$-cycloalkyl or phenyl which phenyl is optionally substituted with halogen, $CF_3$, $OCF_3$, CN, $NO_2$, OH, $C_{1-4}$-alkyl, $C_{1-4}$-alkoxy or $SO_2R^4$; and ...... is a single or double bond; or a pharmaceutically acceptable salt thereof.

2. A compound according to claim 1, wherein $R^1$ is H, straight or branched $C_{1-5}$-alkyl, straight or branched $C_{2-5}$-alkenyl or straight or branched $C_{2-5}$-alkynyl; and $R^2$ is H, straight or branched $C_{1-10}$-alkyl, straight or branched $C_{2-10}$-alkenyl, straight or branched $C_{2-10}$-alkynyl, phenyl optionally substituted with halogen, $CF_3$, CN, $NO_2$, OH, $C_{1-4}$-alkyl, $C_{1-4}$-alkoxy or $SO_2R^4$ wherein $R^4$ is $C_{1-4}$-alkyl or $R^2$ is $C_{1-5}$-alkyl, $C_{2-5}$-alkenyl or $C_{2-5}$-alkynyl each of which is substituted with phenyl which phenyl is optionally substituted with halogen, $CF_3$, $OCF_3$, CN, $NO_2$, OH, $C_{1-4}$-alkyl, $C_{1-4}$-alkoxy or $SO_2R^4$; or a pharmaceutically acceptable salt thereof.

3. A compound according to claim 1, wherein n is 0.

4. A compound according to claim 1, wherein n is 1.

5. A compound according to claim 1 which is selected from the following:

5,6,7,8-Tetrahydro-1,2,5-thiadiazolo[3',4':4,5]thieno[3,2-c]pyridine;

8-Methyl-6,7,8,9-tetrahydro[1,2,5]thiadiazolo[3',4':2,3] thiopyrano-[4,5-c]pyridine;

5-Phenyl-5H-8-methyl-6,7,8,9-tetrahydro[1,2,5] thiadiazolo[3',4':2,3]thiopyrano[4,5-c]pyridine; or a pharmaceutically acceptable salt thereof.

6. A pharmaceutical composition comprising a compound according to claim 1 together with a pharmaceutically acceptable carrier or diluent.

7. The pharmaceutical composition according to claim 6 in the form of an oral dosage unit or parenteral dosage unit.

8. The pharmaceutical composition according to claim 7, wherein the dosage unit comprises from about 1 to about 100 mg of the compound.

9. A method of treating a disease in the central nervous system caused by malfunctioning of the muscarinic cholinergic system comprising administering to a subject in need thereof an effective amount of a compound according to claim 1.

10. A method of treating a disease in the central nervous system caused by malfunctioning of the muscarinic cholinergic system comprising administering to a subject in need thereof a pharmaceutical composition according to claim 6.

11. A compound of formula I

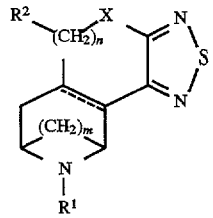

wherein

X is —S—;

m is 2;

n is 0 and $R^2$ is not present;

$R^1$ is H, straight or branched $C_{1-5}$-alkyl, straight or branched $C_{2-5}$-alkenyl, straight or branched $C_{2-5}$-alkynyl, $C_{3-6}$-cycloalkyl or $C_{3-6}$-cycloalkyl-$C_{1-3}$-alkyl; and ...... is a single or double bond; or a pharmaceutically acceptable salt thereof.

12. A compound according to claim 11, wherein $R^1$ is H, straight or branched $C_{1-5}$-alkyl, straight or branched $C_{2-5}$-alkenyl or straight or branched $C_{2-5}$-alkynyl;

or a pharmaceutically acceptable salt thereof.

13. A compound according to claim 11 which is 6,8-Ethano-7-merhyl-5,6,7,8-tetrahydro-1,2,5-thiadiazolo[3',4':4,5]thieno[3,2-c]pyridine or a pharmaceutically acceptable salt thereof.

14. A pharmaceutical composition comprising a compound according to claim 11 together with a pharmaceutically acceptable carrier or diluent.

15. The pharmaceutical composition according to claim 14 in the form of an oral dosage unit or parenteral dosage unit.

16. The pharmaceutical composition according to claim 15, wherein the dosage unit comprises from about 1 to about 100 mg of the compound.

17. A method of treating a disease in the central nervous system caused by malfunctioning of the muscarinic cholinergic system comprising administering to a subject in need thereof an effective amount of a compound according to claim 11.

18. A method of treating a disease in the central nervous system caused by malfunctioning of the muscarinic cholinergic system comprising administering to a subject in need thereof a pharmaceutical composition according to claim 14.

19. A compound of formula I (I)

wherein
X is —S—;
m is 2;
n is 0 and $R^2$ is not present;
q is 1; and
⋯⋯ is a single or double bond; or
a pharmaceutically acceptable salt thereof.

20. A compound according to claim 19 which is 5,9-Methano-5,6,7,8,9,10-hexahydro-1,2,5-thiadiazolo[3',4':4,5]thieno[3,2-c]azocine or a pharmaceutically acceptable salt thereof.

21. A pharmaceutical composition comprising a compound according to claim 19 together with a pharmaceutically acceptable carrier or diluent.

22. The pharmaceutical composition according to claim 21 in the form of an oral dosage unit or parenteral dosage unit.

23. The pharmaceutical composition according to claim 22, wherein the dosage unit comprises from about 1 to about 100 mg of the compound.

24. A method of treating a disease in the central nervous system caused by malfunctioning of the muscarinic cholinergic system comprising administering to a subject in need thereof an effective amount of a compound according to claim 19.

25. A method of treating a disease in the central nervous system caused by malfunctioning of the muscarinic cholinergic system comprising administering to a subject in need thereof a pharmaceutical composition according to claim 21.

26. A method of treating a disease in the central nervous system caused by malfunctioning of the muscarinic cholinergic system comprising administering to a subject in need thereof an effective amount of 6,7,8,9-tetrahydro[1,2,5]thiadiazolo[3,4-h]isoquinoline or a pharmaceutically acceptable salt thereof.

* * * * *